US009637599B2

(12) United States Patent
Roth et al.

(10) Patent No.: US 9,637,599 B2
(45) Date of Patent: May 2, 2017

(54) IMPRINTED BIOMIMETIC CATALYSTS FOR CELLULOSE HYDROLYSIS

(75) Inventors: Stephen Roth, Gladwyne, PA (US); Daeyeon Lee, Wynnewood, PA (US)

(73) Assignees: The Trustees of the University of Pennsylvania, Philadelphia, PA (US); Stephen Roth, Gladwyne, PA (US)

( * ) Notice: Subject to any disclaimer, the term of this patent is extended or adjusted under 35 U.S.C. 154(b) by 549 days.

(21) Appl. No.: 13/259,912

(22) PCT Filed: Mar. 2, 2010

(86) PCT No.: PCT/US2010/025912
§ 371 (c)(1),
(2), (4) Date: Feb. 13, 2012

(87) PCT Pub. No.: WO2010/110998
PCT Pub. Date: Sep. 30, 2010

(65) Prior Publication Data
US 2012/0136180 A1 May 31, 2012

Related U.S. Application Data

(60) Provisional application No. 61/163,323, filed on Mar. 25, 2009, provisional application No. 61/232,180, filed on Aug. 7, 2009.

(51) Int. Cl.
| | | |
|---|---|---|
| C07C 29/00 | (2006.01) | |
| C08G 77/02 | (2006.01) | |
| B01J 21/08 | (2006.01) | |
| B01J 31/02 | (2006.01) | |
| B01J 31/06 | (2006.01) | |
| B01J 37/00 | (2006.01) | |
| C12P 7/10 | (2006.01) | |
| C13K 1/02 | (2006.01) | |
| B01J 31/10 | (2006.01) | |

(52) U.S. Cl.
CPC .............. *C08G 77/02* (2013.01); *B01J 21/08* (2013.01); *B01J 31/0225* (2013.01); *B01J 31/0277* (2013.01); *B01J 31/0284* (2013.01); *B01J 31/067* (2013.01); *B01J 31/069* (2013.01); *B01J 37/0018* (2013.01); *C12P 7/10* (2013.01); *C13K 1/02* (2013.01); *B01J 31/10* (2013.01); *B01J 2231/40* (2013.01); *B01J 2531/96* (2013.01); *C12P 2203/00* (2013.01); *Y02E 50/16* (2013.01)

(58) Field of Classification Search
USPC ........................................................ 568/902
See application file for complete search history.

(56) References Cited

U.S. PATENT DOCUMENTS

| 6,310,110 | B1* | 10/2001 | Markowitz et al. ............ 521/99 |
| 6,884,842 | B2 | 4/2005 | Soane et al. |
| 7,122,122 | B2* | 10/2006 | Marquez-Sanchez et al. ............ 210/663 |
| 2007/0161095 | A1 | 7/2007 | Gurin |

FOREIGN PATENT DOCUMENTS

JP 2006088041 A 4/2006

OTHER PUBLICATIONS

Wei, Y. et al., "A Non-Surfactant Templating Route to Mesoporous Silica Materials," Advanced Materials, 1998, pp. 313-316, vol. 3, No. 4.
Office Action & Search Report, dated Mar. 18, 2014, for copending Chinese Patent Application No. 201080022559.4.
Office Action, dispatch date of Jul. 29, 2013, for copending Japanese Patent Application No. 2012-502074.
Gupta et al., "Molecular Imprinting in sol-gel matrix," Jul. 4, 2008, Biotechnology Advances, 26:533-547.
Katz et al., "Molecular imprinting of bulk, microporous silica," Jan. 20, 2000, Nature, 403:286-289.
Katz et al., "The First Single-Step Immobilization of a Calix-[4]-arene onto the Surface of Silica," Jul. 4, 2002, Chem. Mater., 14:3364-3368.
Bootsma et al., "Cellobiose hydrolysis using organic-inorganic hybrid mesoporous silica catalysts," Apr. 25, 2007, Applied Catalysis A: General, 327:44-51.
Zhu et al., "Dissolution of cellulose with ionic liquids and its application: a mini-review," Mar. 13, 2006, Green Chem., 8:325-327.
Wang et al., "A Room Temperature Ionic Liquid (RTIL)-Mediated, Non-Hydrolytic Sol-Gel Methodology to Prepare Molecularly Imprinted, Silica-Based Hybrid Monoliths for Chiral Separation," 2006, Adv. Mater., 18:3266-3270.
Swatloski et al., "Dissolution of Cellose with Ionic Liquids," Feb. 1, 2002, J. Am. Chem. Soc., 124:4974-4975.
Written Opinion of the International Search Authority for PCT/US10/25912, dated Jun. 2, 2010.
Davis, et al., "Rational Catalyst Design via Imprinted Nanostructured Materials," Chem. Mater., 1996, 8:1820-1839.
Motherwell, et al., "A study of some molecularly imprinted polymers as protic catalysts for the isomerization of α-pinene oxide to trans-carveol," Tetrahedron, 2004, 60:3231-3241.
Bootsma, et al., "Cellobiose hydrolysis using organic-inorganic hybrid mesoporous silica catalysts," Applied Catalysis A: General, 2007, 327:44-51.
Heilmann, et al., "Selective Catalysis on Silicon Dioxide with Substrate-Specific Cavities," Angew. Chem. Int. Ed. Engl., 1994, 33(4):471-473.
Supplementary European Search Report for Application No. EP 10 75 6550, dated Jul. 27, 2012.

\* cited by examiner

Primary Examiner — Yong Chu
Assistant Examiner — Sonya Wright
(74) Attorney, Agent, or Firm — Saul Ewing LLP; Kathryn Doyle; Domingos J. Silva

(57) ABSTRACT

The present disclosure describes methods and biomimetic catalysts useful for hydrolyzing glucose polymers, such as cellulose, and oligomers, such as cellobiose, to glucose for the subsequent production of ethanol.

9 Claims, 4 Drawing Sheets

IMPRINTED BIOMIMETIC CATALYSTS FOR CELLULOSE HYDROLYSIS

CROSS-REFERENCE TO RELATED APPLICATION

The present application is a 35 U.S.C. §371 national phase application from, and claiming priority to, International Application No. PCT/US2010/25912, filed Mar. 2, 2010, and published under PCT Article 21(2) in English, which is entitled to priority under 35 U.S.C. §119(e) to U.S. Provisional Applications No. 61/163,323, filed Mar. 25, 2009, and No. 61/232,180, filed Aug. 7, 2009, all of which applications are hereby incorporated by reference herein in their entireties.

STATEMENT REGARDING FEDERALLY SPONSORED RESEARCH OR DEVELOPMENT

This invention was made with government support under Grant No. CBET 1033017, awarded by the National Science Foundation. The U.S. Government therefore has certain rights in this invention.

BACKGROUND OF THE INVENTION

Refined petroleum products have been a major energy source for many decades. Unfortunately, the prices for both refined and crude petroleum based products have risen dramatically in recent years due to excess demand and dwindling supply. Moreover, petroleum products, when burned, contribute substantially to the ongoing global warming crisis. As a result of the many issues associated with petroleum products, there is substantial interest in exploring alternative energy sources. One alternative to petroleum-based fuel is ethanol.

Ethanol is typically produced by yeast fermentation of either sucrose or glucose, the structures of which are shown in FIG. 1. (Wang, M., et al. *Effect of Fuel Ethanol Use on Fuel-Cycle Energy and Greenhouse Gas Emission*; Argonne National Laboratory: Argonne, 1999.). The viability of replacing petroleum-based fuels with ethanol has already been successfully demonstrated. In Brazil, for example, sugar cane-derived ethanol has largely replaced petroleum-based fuels. (Sperling, D.; Gordon, D., *Two billion cars: driving toward sustainability*. Oxford University Press: New York, 2009.).

Although ethanol has shown promise as an alternative fuel source, there are many obstacles that have hampered the growth of ethanol production in the United States. Specifically, the raw materials necessary to produce ethanol, e.g., sucrose and glucose, are common food stuffs. Sucrose, for example, is a non-reducing disaccharide consisting of glucose and fructose, and is produced primarily from cane sugar or sugar beets. Glucose, produced by the hydrolysis of plant starches (repeating polymers of α-linked glucosides), is derived predominantly from corn. The demand for the raw materials necessary to produce ethanol competes with the demand for food, resulting in increased prices for both food and fuel. The potential benefits of ethanol derived from corn are further diminished by studies that have shown that corn-based ethanol could have a net climate warming effect. (Crutzen, P. J., et al., *Atmospheric Chemistry and Physics* 2008, 8, (2), 389-395.)

In an attempt to mitigate some of the issues related to the production corn-based ethanol, the ethanol industry has turned its attention to methods of developing glucose from cellulose. Cellulose is a polymer consisting of β-1,4-linked glucosides and can be found in nearly all plant materials. Thus, an efficient method of hydrolyzing cellulose into glucose could allow ethanol production facilities to access the estimated $10^{11}$ tons per year of cellulose normally produced by plants on earth.

Large amount of cellulose could even be obtained from crop remains such as corn stover, cane bagasse, and even cellulose-based trash. These materials would be sustainable, easy to collect, and very inexpensive (Saha, B. C., et al. In *Fuel ethanol production from corn fiber—Current status and technical prospects*, 1998; Humana Press Inc: 1998; pp 115-125; Tucker, M. P., et al. In *Conversion of distiller's grain into fuel alcohol and a higher-value animal feed by dilute-acid pretreatment*, 2004; Humana Press Inc: 2004; pp 1139-1159.). Another advantage of cellulose over cane sugar is that cellulose hydrolysis will yield only glucose, which yeast favor over sucrose.

Even though cellulose is easily the most abundant biological material on earth, it is not trivial to hydrolyze cellulose directly to glucose. Given the difficulties associated with the hydrolysis, most efforts at large-scale cellulose hydrolysis have been focused on using cellulases, a class of enzymes that catalyze the hydrolysis of cellulose. Research has also focused on the preparation of modified enzymes engineered to be more stable under the extreme high temperatures and pH conditions required to hydrolyze cellulose. (Sun, Y. et al. *Bioresource Technology* 2002, 83, (1), 1-11; Wright, J. D. *Chemical Engineering Progress* 1988, 84, (8), 62-74.)

Despite some success in preparing cellulases capable of hydrolyzing cellulose to glucose, even the most heat-stable cellulases are expensive and relatively short-lived. Moreover, enzyme-based hydrolysis typically requires several days to achieve desirable reactions. It is also difficult to separate and reuse cellulase enzymes, making any process using these reagents more expensive. The combination of these various issues greatly impedes the economical production of ethanol from lignocellulosic material. It would therefore be useful to develop and use one or more inorganic catalysts that can mimic an exoglucosidase (an enzyme that cleaves a terminal glucose residue from a cellulose oligo- or polysaccharide) and/or an endoglucosidase (an enzyme that cleaves the glucose polymer at an internal linkage).

Inorganic catalysts, unlike their biological counterparts, can successfully tolerate harsh conditions and can be used repeatedly without loss of activity. Moreover, even if an inorganic catalyst were less active then presently known enzymes, the inorganic catalyst could have significant commercial importance. For example, a silica-based zeolite 100 times less active than a corresponding enzyme, but 1000 times less expensive to produce, and 100 times more stable under the conditions necessary for cellulose hydrolysis, would be a commercially attractive alternative to enzyme based technology.

Recent efforts to prepare inorganic catalysts for various purposes have focused on a strategy employing molecular imprinting. (Gupta, R., et al. *Biotechnology Advances* 2008, 26, (6), 533-547; Katz, A., et al. *Nature* 2000, 403, (6767), 286-289.) In molecular imprinting, an imprinting template acts as a form around which cross-linkable monomers are co-polymerized to form a cast-like shell. Without wishing to be bound by any particular theory, it is believed that the monomers in a given imprinting reaction form a complex with the template through covalent and/or non-covalent interactions. The monomers are subsequently polymerized in the presence of the template.

After polymerization, the imprinting template is removed, exposing cavities that are complementary to the template in size and shape. These cavities, essentially negative images of the imprinting templates, are subsequently capable of selectively rebinding the templates, or molecules similar to the templates. The template-free polymer or copolymer can be referred to as a "molecularly imprinted polymer" ("MIP"). MIPs possess the most important features of biological receptors-recognition.

MIPs can comprise cross linked polymers, as described above. They can also comprise amorphous metal oxides or zeolites. Metal oxides and zeolites can be imprinted using a variety of known techniques. In some cases, the cavities or pores produced are an induced fit for polymers of the imprinting molecules. These polymers can subsequently be hydrolyzed by the MIP using the appreciable thermal energy that the imprinted structures can withstand.

A wide variety of templates are suitable for preparing MIPs including, but not limited to, pharmaceuticals, pesticides, amino acids, peptides, nucleotide bases, steroids, and sugars. Derivatives of the target molecule can be used as a template. These derivatives typically mimic the three dimensional structure and functionality of the parent target molecule, but result in MIPs with improved properties. Examples of improved properties include, but are not limited to increased rates of catalysis, longer catalyst life, increased stability at high temperature, or increased stability at various pHs.

There are currently at least four approaches to molecular imprinting. These techniques use various molecules for imprinting, including substrate analogues, transition state analogues, product analogues, and cofactors.

The use of a substrate analogue involves the use of a compound that mimics the reaction complex between the substrate and the matrix. Catalytic groups are introduced in the site by 'baiting' them with the print species and will subsequently act catalytically upon binding of the true substrate. Substrate inhibition can be avoided as the bait molecule may bear little resemblance to either reaction species. An early attempt at using this strategy was the preparation of imprinted matrices with esterolytic activity. In these matrices, cobalt(II) ions were used to coordinate catalytically active vinylimidazole groups and the template during the imprinting process. Subsequent introduction of the substrates (p-nitrophenyl esters of methionine or leucine) to the sites resulted in accelerated and substrate-specific hydrolysis of activated amino acid analogues.

This strategy has also been evaluated to study the mechanism involved in the dehydrohalogenation of α-fluoroketones. In this reaction, the imprinted-matrix facilitated catalysis led to an increase in dehydrofluorination rate compared with the solution reaction by a factor of about 600 (calculated by $k_{cat}/k_{uncat}$ wherein $K_{cat}$=where rate of the catalyzed reaction and $k_{uncat}$ is the rate of the uncatalyzed reaction). The same reaction could also be achieved by the reverse system, in which a carboxylic acid print molecule was used as bait for positioning amino groups in the polymer.

The isomerization of benzisoxazoles has also been studied. In this study, indole was used as a substrate analogue for positioning pyridinyl groups in a matrix. The resulting matrix was shown to be remarkably efficient, with a rate enhancement $[(k_{cat}/K_M)/k_{uncat}]$ of 40,000 over the catalyzed solution reaction. A substrate strategy has also been employed for the dinitrophenolysis of benzoic anhydrides, in which the corresponding benzamide was used as a template.

Another approach to catalysis by molecularly imprinted materials is the use of transition state analogues (TSAs) as templates. When using transition state analogues, the recognition site of the matrix is designed to stabilize the transition state of a given reaction, thereby lowering the transition energy of the reaction and leading to an enhanced reaction rate. For example, the transition state of ester hydrolysis can be mimicked by phosphonate derivatives, a feature that has been used in the preparation of several molecularly imprinted materials.

The TSA approach was followed when a phosphonate ester was imprinted using a polymerizable amidine derivative. The catalyst was tested on the hydrolysis of carboxylic acid esters analogous to the phosphonate esters, resulting in enhanced catalytic efficiencies. The relative reaction rate was 100 times higher for the imprinted matrices compared with the uncatalyzed solution reaction and five times more efficient than for a reference polymer.

Product analogues have also been used as templates in a number of cases. Catalytic polymers prepared using these templates, however, can be sensitive to inhibition. Choice of appropriate templates, though, can overcome this inhibition. For example, product analogues have been used as templates to create catalysts for a Diels-Alder reaction between tetrachlorothiophene dioxide and maleic anhydride.

The Diels-Alder reaction has an inherent entropic barrier and, for efficient catalysis to occur, sufficient stabilization of the diene and dienophile needs to be accomplished. In this study, a product analog, chlorendic anhydride, was used a template in the imprinting protocol. As a result of the judicious choice of a template, the inhibition was minimized. The resulting matrices enhanced the rate of the Diels-Alder reaction about 270-fold.

Another strategy is the use of imprinted cofactors. Natural enzymes frequently use cofactors to enable efficient catalysis because the protein(s) being acted upon are often devoid of side chains carrying reactive electrophilic groups. The cofactors enable group transfer reactions. In addition, cofactors can easily be transported to a location where they are needed. Such cofactors may involve metal ions that can act as Lewis acids in, for example, facilitating polarization of carbonyl groups and binding water molecules. In addition, coenzymes can facilitate a number of reactions, such as redox processes, (de)carboxylations and transaminations.

For example, the chemistry involved in enzymatic reactions using the coenzyme pyridoxalphosphate, common to many enzymes, was employed in an imprinting protocol. N-pyridoxyl-L-phenylalanine anilide was used as the template. The resulting imprinted polymer was analyzed for its ability to catalyze the formation of adducts between free pyridoxal and phenylalanine. An eightfold rate enhancement was recorded compared with a reference polymer.

An example of metal-coordination-assisted catalysis has been reported in the preparation of a class II aldolase mimic. A complex of an analogue of a reactive intermediate product (dibenzoylmethane) with cobalt(II) ions was imprinted in conjunction with 4-vinylpyridine in a polystyrene-based copolymer system. The polymer was capable of catalyzing the condensation of acetophenone and benzaldehyde to produce chalcone and the resulting activity was eight times higher than the solution reaction. Substrate selectivity and true turnover could be recorded.

In addition to the above discussed embodiments, studies have also demonstrated that mesoporous organic-inorganic silica catalysts can be used for hydrolysis of subunits of cellulose. See, e.g. Bootsma, J. A., et al., *Applied Catalysis a-General* 2007, 327, (1), 44-51 and Bootsma, J. A., et al.,

*Bioresource Technology* 2008, 99, (12), 5226-5231. The activation energy of the processes described in these references was found to be similar to those reported for cellulose hydrolysis reactions using homogeneous organic acids. Although these studies show the feasibility of using inorganic catalysts for hydrolysis of cellulose, the silica catalysts described in these references lack the specificity of natural enzymes and cause substantial degradation of cellulose subunits to compounds other than glucose.

Thus, in order to achieve mass production of ethanol from cellulose, there is a long felt, but unmet need for scalable, chemically robust, and economical processes to hydrolyze cellulose to glucose for subsequent fermentation. The present invention meets this need.

BRIEF SUMMARY OF THE INVENTION

The present invention is directed to an imprinted mesoporous silica catalyst capable of binding and hydrolyzing at least one glucose substrate to glucose. The present invention further includes methods of preparing this catalyst as well as methods for using this catalyst for a hydrolysis reaction.

In certain embodiments, the invention can comprise a biomimetic catalyst. The catalyst can comprise a polymeric silica matrix, at least one active site imprinted into said matrix, and at least one acidic functionality in said active site.

In certain embodiments, the at least one acidic functionality is selected from the group consisting of a phenol, a carboxylic acid, and a sulfonic acid.

In some embodiments, the active site is capable of binding at least one glucose substrate.

The present invention further includes a method for preparing a biomimetic catalyst. The method includes the steps of reacting at least one tetraorthosilicate with at least one silane in the presence of an imprinting molecule to form a polymeric silica matrix impregnated with said imprinting molecule. At least 1 mol percent of said at least one silane is an acid functionalized silane. The method further includes isolating the impregnated polymeric silica matrix; and removing said imprinting molecule via washing or burning to form a silica matrix imprinted with the structure of said imprinting molecule.

In certain embodiments, the at least one tetraorthosilicate is selected from the group consisting of Formulas I, II, III, and IV:

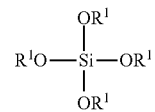

Formula I

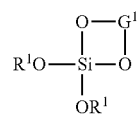

Formula II

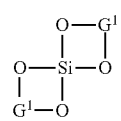

Formula III

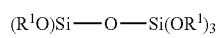

Formula IV wherein $R^1$ is, independently at each occurrence, $C_1$-$C_6$ alkyl or phenyl; $G^1$ is $C_1$-$C_6$ alkyl,

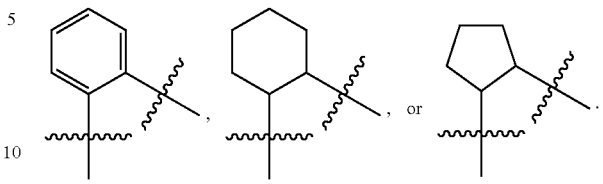

In certain embodiments, $R^1$ is $CH_2CH_3$ at each occurrence.

In certain embodiments, the at least one silane is a compound according to one of Formulas V, VI, or VII:

Formula V

Formula VI

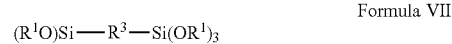

Formula VII wherein $R^1$ is, independently at each occurrence, $C_1$-$C_6$ alkyl or phenyl; $R^2$ is, independently at each occurrence,

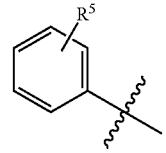

or $C_1$-$C_6$ alkyl optionally substituted with at least one substituent selected from the group consisting $R^4$ and

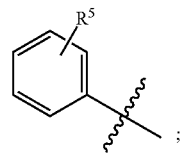

$R^3$ is $C_1$-$C_6$ alkyl optionally substituted with a substituent selected from the group consisting of $R^4$ and

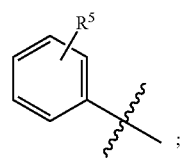

$R^4$ is SH, $NH_2$, OH, $CO_2H$, or $SO_3H$; and $R^5$ is H, $NH_2$, OH, $SO_2Cl$, $CO_2H$, or $SO_3H$; provided that when $R^4$ is SH or $R^5$ is $SO_2Cl$, the thiol or chlorosulfonyl groups are oxidized to $SO_3H$ after said removing of said imprinting molecule.

The present invention further provides a method for the production of glucose, said method comprising dissolving a glucose substrate in a solvent and contacting said glucose substrate in said solvent with at least one biomimetic catalyst to hydrolyze said glucose substrate to glucose. In this embodiment, the biomimetic catalyst comprises a polymeric silica matrix, at least one active site imprinted into said matrix, and at least one acidic functionality in said active site; and In certain embodiments, the solvent is an ionic liquid or molten salt.

The present invention further includes a method for preparing a biomimetic catalyst, said method comprising reacting at least one tetraorthosilicate with at least one functionalized imprinting molecule and optionally, at least one silane, to form a polymeric silica matrix impregnated with said functionalized imprinting molecule; isolating said polymeric silica matrix so impregnated; and removing said imprinting molecule from said polymeric silica matrix so impregnated via hydrolysis or burning to form a silica matrix imprinted with the structure of said imprinting molecule.

In certain embodiments, said at least one tetraorthosilicate is selected from the group consisting of Formulas I, II, III, and IV as shown above, wherein $R^1$ is, independently at each occurrence, $C_1$-$C_6$ alkyl or phenyl; $G^1$ is $C_1$-$C_6$ alkyl,

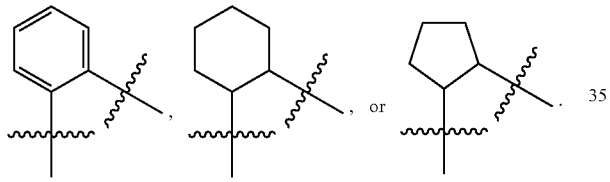

In certain embodiments, $R^1$ is $CH_2CH_3$ at each occurrence.

In other embodiments, the at least one silane is a compound according to one of Formulas V, VI, or VII as shown above wherein $R^1$ is, independently at each occurrence, $C_1$-$C_6$ alkyl or phenyl; $R^2$ is, independently at each occurrence,

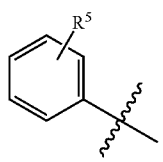

or $C_1$-$C_6$ alkyl optionally substituted with at least one substituent selected from the group consisting $R^4$ and

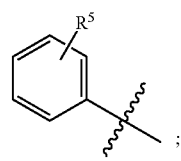

$R^3$ is $C_1$-$C_6$ alkyl optionally substituted with a substituent selected from the group consisting of $R^4$ and

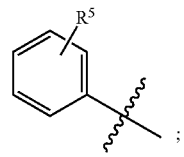

$R^4$ is $NH_2$, OH, $CO_2H$, or $SO_3H$; and $R^5$ is H, $NH_2$, OH, $CO_2H$, or $SO_3H$.

In other embodiments, the functionalized imprinting molecule comprises an imprinting molecule functionalized with at least one poly-functionalized linker selected from the group consisting of Formulas VIII, IX, X, and XI:

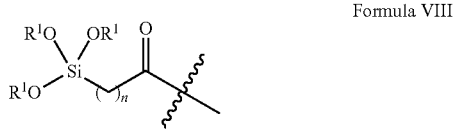

Formula VIII

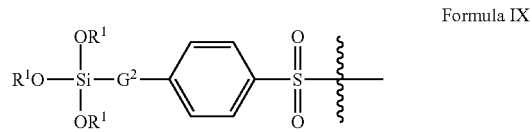

Formula IX

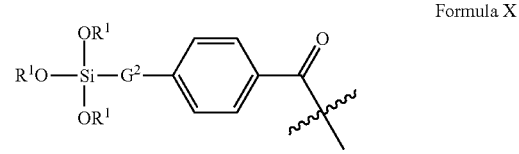

Formula X

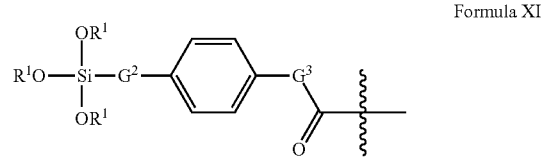

Formula XI wherein, $R^1$ is, independently at each occurrence, $C_1$-$C_6$ alkyl or phenyl; $G^2$ is $C^1$-$C^6$ alkyl, provided that $G^2$ is optional, such that when $G^2$ is absent, a single bond is formed between the carbon and silicon shown linked to $G^2$; and $G^3$ is N or O.

In certain embodiments, the silane is not optional and said tetraorthosilicate, silane, and functionalized imprinting molecule are present in a ration of from about 100:20:80 to about 100:95:5.

The present invention further includes a method for the production of ethanol, said method comprising dissolving a glucose substrate in a solvent; contacting said glucose substrate in said solvent with at least one biomimetic catalyst to completely or partially hydrolyze said glucose substrate to glucose; isolating said glucose; and converting said glucose to ethanol. The biomimetic catalyst can comprise a polymeric silica matrix; at least one active site imprinted into said matrix, and at least one acidic functionality in said active site.

The present invention further includes a method for preparing a functionalized imprinting molecule, said method comprising reacting an imprinting molecule with a poly-functionalized linker precursor; and isolating said functionalized imprinting molecule.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE INVENTION

Figure 1:
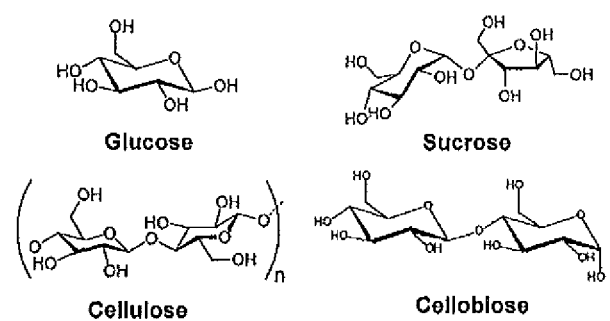
FIG. 1 depicts the structures of cellulose, glucose, fructose, and cellobiose as known in the prior art.
Figure 2:
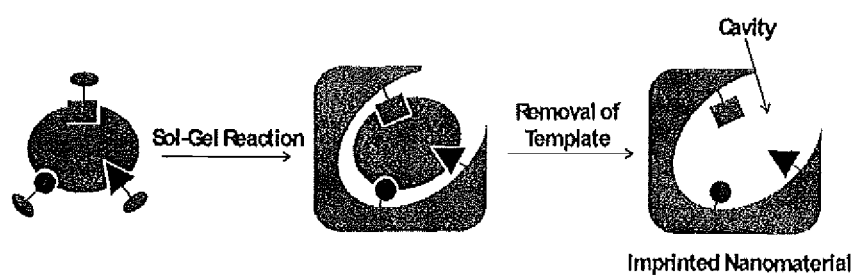
FIG. 2 is a schematic representation of molecular imprinting using sol-gel chemistry.

The present invention includes novel MIPs and methods of preparing these structures for the eventual catalytic hydrolysis of cellulose or a cellulose derivative. In certain embodiments, the MIP comprises an amorphous metal oxide and/or zeolite that has been imprinted with a glucose substrate. In certain embodiments, the MIP can additionally be imprinted with endoglucosidase, exoglucosidase, and/or a transition state analogue of glucosidase.

The MIPs prepared as described herein can be manufactured in a powdered form, such that when mixed with a glucose substrate under conditions that render the glucose substrate soluble or partially soluble, the glucose substrate can be hydrolyzed by the MIP.

In an embodiment of the preparative method described herein, a cross-linkable monomer is polymerized in the presence of one or more imprinting molecules. At least one monomer is present for polymerization, and in certain instances, one or more additional co-monomers can be present. The presence of the imprinting molecules during polymerization gives rise to the formation of imprints, or memory sites, within the resulting MIP. The size and shape of the imprints are complementary to the size and shape of the imprinting molecule. Removal of the imprinting molecules from the resulting polymer provides the MIP described herein.

The MIP described herein can behave as an enzyme mimic, wherein the MIP can hydrolyze β-1,4 glycosidic linkages at a rate exceeding the rate at which β-1,4 glycosidic linkages are spontaneous hydrolyzed under identical conditions but without catalyst. In one embodiment of the invention, the MIP acts like an exoglucosidase. In another aspect of the invention, the MIP can bind a glucose substrate. In yet another aspect of the invention, the MIP comprises a nanostructured zeolite. In still another aspect of the invention, the MIP comprises an amorphous metal oxide.

In another embodiment of the invention the MIP acts like an endoglucosidase. In one aspect of the invention, the MIP can bind a glucose substrate. In yet another aspect of the invention, the MIP comprises a nanostructured zeolite. In still another aspect of the invention, the MIP comprises an amorphous metal oxide.

The present invention also includes a composition comprising an MIP that behaves as an enzyme mimic, wherein the MIP hydrolyzes β-1,4 glycosidic linkages at a rate that exceeds the rate of spontaneous β-1,4 glucose bond hydrolysis under identical conditions but without MIP catalyst present. In one embodiment of the invention, the MIP binds a glucose substrate. In another embodiment of the invention, the MIP binds a transition state analogue of glucosides linked to agylcones. In one aspect of the invention, the MIP comprises a nanostructured zeolyte. In another aspect of the invention, the MIP comprises an amorphous metal oxide.

The present invention also includes a composition comprising a MIP that shifts reaction equilibrium towards product formation. In one embodiment, the MIP comprises an adsorbent molecularly imprinted with a reaction product, wherein the adsorbent acts to remove freshly produced product in a reversible and recoverable manner. In one aspect, the MIP comprises a polymer imprinted with one or more substrates selected from group consisting of an imprinting molecule and for a transition state hexose. In another aspect, the MIP comprises a molecularly imprinted polymer hydrogel. In a preferred aspect, the imprinted hydrogel binds glucose.

The present invention further includes a method of deriving glucose from cellulose, the method comprising using a molecularly imprinted polymer (MIP), wherein the MIP hydrolyzes β-1,4 glycosidic linkages. In one embodiment of the invention, the method comprises adding to a reaction an MIP that mimics an exoglucosidase. In another embodiment of the invention, the method comprises adding to a reaction an MIP that mimics an endoglucosidase. In one aspect of the invention, the MIP binds a glucose substrate and/or a transition state analogues of glucosides linked to agylcones.

The invention further includes a method of deriving glucose from cellulose wherein multiple MIPs are combined in a single reaction, wherein each of the MIPs acts as a different component of the reaction. In one embodiment of the method of the invention, one or more MIPs are added to a reaction wherein cellulose is converted to glucose, wherein the MIPs act as an exoglucosidase. In another aspect, additional MIPs are added to the same reaction, wherein the MIPs act as an endoglucosidase. In yet another embodiment of the invention, adsorbant MIPs are added to the same reaction, wherein reaction equilibrium shifts towards product formation. In a preferred aspect of the invention, the adsorbant MIP reversibly adsorbs the product, wherein the product is glucose.

In a further embodiment, the present invention is directed to an imprinted mesoporous silica catalyst capable of binding and hydrolyzing at least one glucose substrate to glucose. The present invention further includes methods of preparing this catalyst as well as methods for using this catalyst for a hydrolysis reaction. The invention therefore provides compositions and methods that convert cellulose to glucose using non-enzymatic hydrolysis in a process that mimics the activity (and potentially specificity) of natural enzymes that catalyze this process.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The phrase "imprinting molecule" as used herein refers to polymeric, oligomeric, and monomeric compounds that can be used for preparing imprinted catalysts capable of hydrolyzing certain glucose substrates to glucose. Examples of imprinting molecules include, but are not limited to, cellulose, cellobiose, linear oligomeric β(1-4) linked glucose chains longer than cellobiose but shorter than cellulose, carboxymethylcellulose, methylcellulose, and hydroxypylcellulose; linear and branched α-linked glucose oligomers and polymers such as, but not limited to, starches, glycogens, amyloses, dextrans, and derivatives thereof; sucrose, lactose, and trehalose; fructans (also called inulins); pectins; glycosaminoglycans; agar, gum Arabic, and karageenan. Imprinting molecules can further include monomeric compounds such as glucose and other known hexoses and pentoses. Glucose derivatives, such as D-glucose 6-phosphate are likewise included, as are other known glucose derivatives.

The phrase "glucose substrate" and variations thereof, refers to polymeric and oligomeric compounds that can be hydrolyzed to glucose using an imprinted catalyst. Examples of glucose substrates include, but are not limited to, cellulose, cellobiose, linear oligomeric β(1-4) linked glucose chains longer than cellobiose but shorter than cellulose, as well as linear and branched α-linked glucose oligomers and polymers such as, but not limited to, starches, glycogens, amyloses, dextrans, and derivatives thereof.

As used herein the designation "$C_x$-$C_y$," alkyl refers to the number of possible carbons in a given alkyl group. For example, the phrase $C_1$-$C_6$ alkyl refers to alkyl groups having from 1 to 6 carbons and includes but is not limited to, for example, methyl, ethyl, n-propyl, n-butyl, n-pentyl, n-hexyl, isopropyl, isobutyl, isopentyl, isohexyl, neopentyl, neohexyl, cyclopropyl, cyclobutyl, cyclopentyl, cyclohexyl, 1-methylpentyl, 2-methylpentyl, 3-methylpentyl, 2-ethylpropyl, and 2-ethylbutyl. Similarly the phrase $C_1$-$C_3$ alkyl refers to alkyl groups having from 1-3 carbons, and includes, for example, methyl, ethyl, propyl, cyclopropyl, and isopropyl.

The phrase "active functionalities" as used herein refers to acidic functionalities, such as, but not limited to, sulfonic acid groups, carboxylic acid groups, and phenol groups.

As used herein, the words "silane" or "silanes" refer collectively to the class of molecules including alkyltrialkoxysilanes and dialkyldialkoxysilanes.

As used herein, "about" encompass variations of ±20% or ±10%, more preferably ±5%, even more preferably ±1%, and still more preferably ±0.1% from the specified value, as such variations are appropriate to perform the disclosed methods.

As used herein, an "MIP" or "molecularly imprinted polymer" refers to a material, such as an organic polymer or copolymer, a silica based polymer, a zeolite, or other material described herein, polymerized or otherwise constructed in the presence of an imprinting template.

Methacrylic Acid-Based Molecularly Imprinted Polymers

MIPs based on methacrylic acid can be made by polymerizing methacrylic acid (wherein the acid serves as an active functionality suitable for cleaving the bonds of a glucose substrate) and a cross linking agent in the presence of an imprinting molecule. In certain embodiments, the ratio of imprinting molecule:methacrylic acid:cross linking agent can be 1:16:80. The ratio can, however, be from about 1:98:1 to about 10:40:40, by mol.

Exemplary cross linking agents include, but are not limited to, acrylates, methacrylates, acrylamides, vinyl ethers, epoxides, methacrylamide, vinylbenzene, α-methylvinylbenzene (alpha-methylstyrene or AMS), divinylbenzene, maleic acid and related derivatives, as well as fumaric acid and related derivative.

Polymerization of methacrylic acid based MIPs can be accomplished by reaction methods described in the texts of L. H. Sperling, Introduction to Physical Polymer Science, Chapter 1, pp. 1-21, John Wiley and Sons, New York, 1986, and R. B. Seymour and C. E. Carraher, Polymer Chemistry, Chapters 7-11, pp. 193-356, Dekker, New York, 1981. The Free-radical mechanism is one example. Both heat and UV can be applied to accelerate polymerization.

The polymeric material can be cross linked in the presence of a cross linking agent by, for example, by heat or radiation, such as UV light. Catalysts in addition to photo- or thermal initiators can also be used to promote crosslinking. Such initiators and catalysts are commercially available. Acrylate chemistry methods known in the art can be used, as described, for example, in U.S. Pat. No. 5,459,176; A. Sassi, Polymer Applications for Biotechnology, (D. Soane ed. Prentice Hall 1992); and Encyclopedia of Polymer Science and Engineering (M. Bikales, Overberger, Menges eds., Wiley 1988), the disclosures of which are incorporated herein by reference. UV light, in conjunction with one or more initiators such as Irgacure™ and/or Darocur™ (Ciba Specialty Chemicals, Tarrytown, N.Y.) can be used to accelerate curing of acrylic or acrylamide cross linkers.

Methods for Producing Methacrylic Acid-Based MIPs

In a typical preparation of the methacrylic acid-based MIPs described herein, the imprinting molecule is mixed with a porogenic solvent. Porogenic solvents are those solvents which are suitable for forming pores and/or displacing polymer chains during polymerization. The characteristics and use of such solvents in the formation of macroreticular or macroporous resins are described in U.S. Pat. No. 4,224,415.

A porogenic solvent is one which dissolves the monomer mixture being copolymerized but which does not dissolve the copolymer. In addition, the porogenic solvents are inert to the polymerization conditions. Examples include toluene, xylene, ethylbenzene, $C_6$-$C_{12}$ saturated aliphatic hydrocarbons like heptane and iso-octane and $C_4$-$C_{10}$ alkanols like tert-amyl alcohol, sec-butanol and 2-ethylhexanol. Aromatic hydrocarbons and $C_6$-$C_{12}$ saturated aliphatic hydrocarbons and their mixtures are also work.

Methacrylic acid is subsequently added and dissolution is aided by sonication, if necessary. Ethylene glycol dimethacrylate (EDMA) and azobisisobutyronitrile (AIBN) are subsequently added. The mixture is cooled in an ice/water bath and sparged with $N_2$ for about 5 minutes.

Once all of the reactants are mixed in the solvent, polymerization can be induced using one of several methods. In certain embodiments, polymerization can be induced using UV radiation at about 366 nm. (CAMAG 23200, Bubendorf, CH). Treatment typically proceed for about 36 to about 48 hours at about 0 to about 20° C. Although higher temperatures can be used, it has been demonstrated that polymers prepared at lower temperatures via irradiation exhibit higher recognition abilities. Without wishing to be bound to any particular theory, it is also thought that weak noncovalent interactions, such as hydrogen bonding, essential for imprint formation and subsequent recognition, are stronger at lower temperatures due to favorable entropy. In other embodiments, polymerization can be induced at 45° C. using ABDV (2,2'-Azobis(2,4-dimethyl)valeronitrile) as a free radical initiator and acetonitrile as solvent.

The above described procedures result in the preparation of a bulk polymer monolith. This polymer monolith can then be ground in a mechanical mortar and wet-sieved. Particles with diameter smaller than 25 μm are collected. Fine particles are removed from the collected particles by repeated sedimentation in acetone or ethanol, and finally dried in a vacuum desiccator.

The imprinting molecule can then be extracted with an appropriate solvent. In certain embodiments, 90:10 methanol:acetic acid solution (v/v), can be used. Depending upon whether or not the imprinting molecule has a chromophore, spectrophotometric monitoring at an appropriate wavelength (i.e. 254 nm) can ensure complete removal. A control or reference polymer can be prepared using the same procedure except that no imprinting molecule is included in the reaction.

Poly(Allylamine)-Derived MIPs

In addition to preparing MIPs from methacrylic acid, MIPs can be prepared from poly(allylamine). In certain embodiments, a poly(allylamine)-derived MIPs can be prepared by combining aqueous poly(allylamine hydrochloride) (PAA-HCl) with an imprinting molecule, such as, for example, D-Glucose 6-phosphate ("GSP"). In certain embodiments, the D-glucose 6-phosphate can be as salt, such as the monobarium salt ("GSP-Ba"). The aqueous poly(allylamine) can be at any concentration, however, preferably, the solution is 25% w/v.

The poly(allylamine) and imprinting molecule can be mixed for an appropriate amount of time to ensure association of the imprinting molecule with the poly(allylamine). A portion of the PAA-HCl is then neutralized with an appropriate base, such as aqueous NaOH. The resulting free amine can then be treated with a cross linking agent, such as epichlorohydrin (EPI), resulting in the formation of a gel.

After gel formation, the resulting MIP is allowed to sit overnight to ensure complete crosslinking. The MIP can then be cut into squares, or any other shape, which can be, for example, about 4 mm at its widest. The square then can be washed with an appropriate base, such as aqueous NaOH, for an appropriate amount of time to ensure complete or nearly complete removal of the imprinting molecule and/or unreacted poly(allylamine) and cross linking agent. The base-washed MIP can then be washed with deionized water to remove any remaining NaOH, while monitoring the effluent wash pH.

Removal of NaOH can be considered sufficient when the effluent solution, after an overnight equilibration period with the gel, is no longer basic (pH<6.5). The resulting MIP can then be dried in an oven at about 50° C.

Removal of the imprinting molecule can be assessed quantitatively. For example, when the imprinting molecule is GSP, the total phosphorous concentration (and thus the molar quantity of D-Glucose 6-phosphate) remaining in the MIP can be determined spectrophotometrically using a Hach D2010 spectrophotometer and Hach's method 8190, which is an acid persulfate digestion method used to determine total phosphorus.

The presence or absence of the GSP imprint can be quantified using the following procedure: A freshly synthesized hydrogel, containing the GSP imprint, can be placed in a known volume of deionized water and stirred for 24 h. A filtered aliquot is taken and diluted appropriately in a volumetric flask for the Hach total phosphorus test. The pH of the diluted sample is checked to ensure that it is between 6.5 and 7.5 and tested for total phosphorus. The phosphorus concentration in the water wash should be less than 7% of what would be expected if all of the GPS used in the synthesis were present in the DI water wash solution. This same polymer is then placed in 4M NaOH solution and stirred for 24 h to remove the bound GSP. A filtered aliquot is then taken and the sample's pH adjusted to be between 6.5 and 7.5 using HCl. The polymer is placed in a fresh 4M NaOH solution and stirred for another 24 hours. This solution is then tested for total phosphorus. The total phosphorus concentration in the base wash is usually 95% of what would be expected upon full GSP-Ba template removal from the imprinted gel.

Glucose substrate binding capacities of poly(allylamine)-derived MIPs are determined via batch reactor studies as described in Wizeman and Kofinas, 2001, Biomaterials 22:1485-91. According to the procedure described therein, MIPs can be added to an aqueous or buffered solution of pure glucose or fructose (at about 50 mg/ml) or to a solution comprising a 1:1 mixture of the two sugars. In certain embodiments, buffered solutions useful for the analysis can be prepared using BBS (N,N-bis[2-Hydroxyethyl]-2-aminoethanesulfonic acid), potassium dihydrogenphosphate ($KH_2PO_4$) and sodium chloride (NaCl).

After combining the test solution and MIP whose binding capacity is to be determined, the mixture can be allowed to equilibrate, with stirring, for about 4 h. Then, filtered aliquots of the test solution are removed to determine the concentration of sugar remaining in the test solution. Using these data, binding capacities can be calculated as described in Wizeman and Kofinas, 2001, Biomaterials 22:1485-91. Glucose concentrations can be determined colorimetrically using a Hach DR2010 spectrophotometer and Stanbio's enzymatic glucose reagent. Fructose concentrations can be determined colorimetrically using a procedure originally developed by Van Creveld and later modified by Oppel (in Browne and Zerban, eds. Physical and Chemical methods of sugar analysis. NY: Wiley; 1941, pg 961).

MIP Catalyst Preparation

For sample preparation, each catalyst is incubated before freeze-drying for about 1-2 minutes at 4° C. in either amphiphile-containing (for imprinted catalyst) or amphiphile-free (for control catalyst) buffer. The buffers used are 10 mM Tris-HCl (containing 0.2 mM $Ca^{2+}$) at pH 8.0 or 7.5. After freeze drying, activated and non-activated samples are washed (stirring the resultant suspension followed by centrifugation) at least three times with an anhydrous solvent (or solvent mixture): typically, anhydrous benzene or benzene/ethanol, 95:5 (v/v) or 90:10 (v/v) or ethyl acetate. The solvent must be selected carefully on the basis of amphiphile solubility and to minimize any deleterious effects on the catalyst. It should be noted that unwashed catalyst preparations yield similar activities in nonaqueous medium when compared to washed controls. After washing, samples are vacuum dried for at least three hours.

Non-Aqueous Assay of MIP Catalysts

A given amount of washed (imprinted or control) catalyst powder is suspended in a given volume of a substrate-containing reaction medium in a stoppered screw-capped vial, sonicated for 10 seconds, and shaken at 250 rpm at 25° C. The reaction progress is monitored by periodically withdrawing 10 ml aliquots of the reaction mixture. The aliquots are treated and analyzed by normal phase HPLC or by reverse phase HPLC. Alternatively, the reactions can be monitored with GC using standard derivatization procedures. In all cases, simultaneous disappearance of substrate and accumulation of product is followed.

Alternatively, tritiated substrate (e.g. specific activity 10-100 Ci/mmol) can be incubated in 1 ml of acetonitrile/acetic acid, 95:5 (v/v) for 15 hrs at room temperature. The polymer particles are then centrifuged (1000×g, 5 min) and radioactivity in 200 μl of the supernatant measured by liquid scintillation counting.

Aqueous Assay

MIP (5 mg) is incubated for 15 hours at room temperature in 1 ml of buffer (e.g. 20 mM sodium citrate, pH 3, 4.5 or 6, 20 mM sodium phosphate, pH 7.3, 20 mM, or sodium carbonate, pH 9.2, containing either 0, 1, 10, or 50% ethanol). After centrifugation, radioactivity in 400 ml of the supernatant was measured by liquid scintillation counting. containing 3 ng of tritiated substrate (e.g. 10-100 Ci/mmol) and competing ligands (ranging from 50 nM to 2 mM).

Silane Based Biomimetic Catalyst

As described elsewhere herein, one strategy to mimic the activity of natural enzymes is the so-called "molecular imprinting" method. In this method, cross-linked polymers, amorphous metal oxides, or zeolites are synthesized in the presence of one or more molecules whose structure(s) are imprinted in the resulting matrix during its formation. Particularly useful cross-linked polymers that are susceptible to imprinting are Si based polymers. These polymers include many Si—O linkages and a smaller percentage of Si—R linkages, wherein R can be variously substituted alkyl, aryl, or other non-oxygen functionality.

In light of the utility of Si based polymers, the catalyst described herein is a polymeric silica matrix that has been imprinted with one or more imprinting molecules, resulting in a catalyst including at least one, and in certain embodiments, a plurality of active sites. The active sites of the catalyst are capable of binding one or more varieties of glucose substrate. Once the active site binds a glucose substrate, active functionalities strategically located within the active site react with the glucose substrate to break or otherwise assist in the breaking of glycosidic bonds.

The silica matrix of the catalyst can be prepared using sol/gel chemistry. One major advantage of molecularly imprinted Si based sol-gel networks over natural or engineered enzymes is superior thermal stability. Silicon based materials can easily withstand the high temperatures and low pHs necessary for hydrolysis of cellulose on an industrial scale. Additional benefits of the Si based catalysts over naturally occurring enzymes include recoverability and cost effectiveness.

The silica matrix can be prepared by polymerizing one or more tetraorthosilicates with one or more silanes. Tetraorthosilicates useful for preparing the silica matrix of the catalyst described herein can have structures according to any of Formulas I, II, III or IV. Silanes useful for the polymerization described herein can have structures according to Formulas V, VI, and VII.

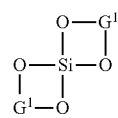

Formula I

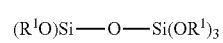

Formula II

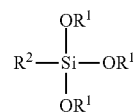

Formula III

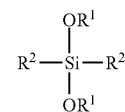

Formula IV (R¹O)Si—O—Si(OR¹)₃

Formula V $$R^2-\underset{\underset{OR^1}{|}}{\overset{\overset{OR^1}{|}}{Si}}-OR^1$$

Formula VI $$R^2-\underset{\underset{OR^1}{|}}{\overset{\overset{OR^1}{|}}{Si}}-R^2$$

Formula VII (R¹O)Si—R³—Si(OR¹)₃

In the formulas above, $R^1$ can be, independently at each occurrence, $C_1$-$C_6$ alkyl or phenyl.

$R^2$ can be, independently at each occurrence, $C_1$-$C_6$ alkyl optionally substituted with at least one substituent selected from the group consisting $R^4$ and

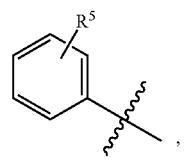

Alternatively, $R^2$ can be

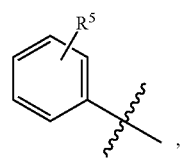

$R^3$ can be $C_1$-$C_6$ alkyl optionally substituted with a substituent selected from the group consisting of $R^4$ and

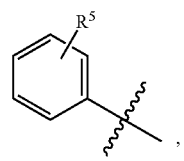

$R^4$ can be SH, NH₂, OH, CO₂H, or SO₃H.

$R^5$ can be H, SO₂Cl, NH₂, OH, CO₂H, or SO₃H.

$G^1$ can be $C_1$-$C_6$ alkyl (such that an optionally $C_1$-$C_5$ alkyl substituted 1,3,2-dioxasiletane, an optionally $C_1$-$C_4$ alkyl substituted 1,3,2-dioxasilolane, or an optionally $C_1$-$C_3$ alkyl substituted 1,3,2-dioxasilinane is formed),

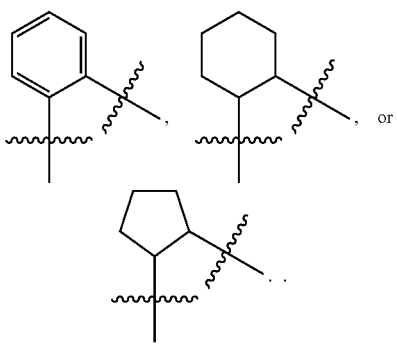

When either $R^4$ is SH or $R^5$ is $SO_2Cl$, the thiol or chlorosulfonyl groups, can be oxidized to $SO_3H$ in order to provide the functional groups appropriate for hydrolyzing a given substrate. When $R^4$ is SH, the oxidant can be, for example, $H_2O_2$. When $R^5$ is $SO_2Cl$, the oxidant can be, for example, water.

The polymerization of the tetraorthosilicate and the silane(s) can be acid or base catalyzed and can takes place in a variety of solvents, including water, standard organic solvents, and ionic liquids. Examples of suitable ionic liquids include, but are not limited to N-ethylpyridinium chloride, $BMIM^+X^-$ ($BMIM^+$=1-butyl-3-methylimidazolium) wherein X=Cl, Br, SCN, $BF_4$, or $PF_6$, and $AMIM^+Cl^-$ (AMIM=1-allyl-3-methylimidazolium chloride). Useful organic solvents include, but are not limited to, N,N-DMF, methanol, ethanol, isopropanol, ethyl acetate, isopropyl acetate, dichloromethane, chloroform, NMP, tetrahydrofuran (THF), acetonitrile, as well as mixtures thereof.

Suitable acidic catalysts include, but are not limited to, anhydrous and aqueous HCl, p-toluenesulfonic acid, sulfuric acid, benzene sulfonic acid, camphor sulfonic acid, and other acids known to those of ordinary skill in the art. Suitable basic catalysts include NaOH, $CaOH_2$, $MgOH_2$, and $NH_4OH$.

Molecular imprinting with an imprinting molecule takes place during the polymerization reaction. In one embodiment of the imprinting process, the imprinting molecule is added directly to the polymerization reaction. The quantity of imprinting molecule added will be dependent on several factors, including the size (molecular weight) and solubility of the imprinting molecule. Anywhere from about 1 to about 99 mol percent of the imprinting molecule including any whole or partial increment therebetween (based on the total molar quantity of silane and tetraorthosilicate) can be added.

At least some of the silane can be functionalized with an acidic group, such as a sulfonic acid, carboxylic acid, or phenol, so that the catalyst produced according to the present method will be able to cleave glycosidic linkages. Examples of acid functionalized silanes include, but are not limited to, those compounds of Formulas V, VI, and VII described previously, as well as compounds such as triethoxysilylpropylmaleamic acid, and N-(trimethoxysilylpropyl)ethylenediamine, triacetic acid, trisodium salt.

In certain embodiments, the quantity of functionalized silane can be from about 1 to about 50 mol percent of the total quantity of silane used to prepare the polymeric material, inclusive of any and all whole or partial increments therebetween, with the remainder being unfunctionalized silane. In specific embodiments, the quantity of functionalized silane can be from about 1 to about 40 percent, from about 1 to about 30 percent, from about 1 to about 25 percent, from about 1 to about 20 percent, from about 1 to about 15 percent, from about 1 to about 10 percent, or from about 1 to about 5 mol percent of total quantity of silane.

For each of the embodiments described above, the polymeric matrix forms around the imprinting molecules present during the polymerization reaction. As a result, the imprinting molecules become impregnated in or on the silica matrix.

Once the polymerization is complete, the solvent in the reaction flask can be removed. Solvent removal can take place before or after a first milling step, depending upon the solubility of the catalyst matrix. When the resulting polymeric matrix is soluble in the reaction solvent, the solvent can be removed under reduced pressure using, for example, a rotary evaporator. Alternatively, solvent can be removed using one of variously known freeze drying techniques. In another embodiment, solvent can be washed away with supercritical $CO_2$. When the resulting silica matrix is not soluble in, or is substantially less soluble in the reaction solvent than the starting materials, the silica matrix material can be filtered away from the reaction solvent.

Although standard evaporative techniques can be used to remove solvent from the reaction vessel, it is not a preferred methodology. Specifically, removing solvent under reduced pressure creates surface tension at or near the newly formed active sites in the silica matrix. This surface tension can damage, shrink, or otherwise deform the matrix during the solvents' liquid/gas transition. Thus, a process which mitigates these potential pitfalls is preferable. One such method is supercritical drying.

Supercritical drying using supercritical $CO_2$ is useful as it mitigates any issues associated with surface tension resulting from a typical volatilization processes. The supercritical $CO_2$ wash can also act to burn off any imprinting molecules present in the matrix if performed at high enough temperature.

The dry solid can then be milled to give silica particles having specific sizes. Upon completion of the milling process, particles can be washed with solvent to remove any imprinting molecules revealed by the process. The particles can then be dried with supercritical $CO_2$. Alternatively, or additionally, the milled solids can be heated to a sufficiently high temperature so that any imprinting molecules present in the milled solids are burned away. Once all of the excess imprinting molecules have been removed, the resultant silica particles can be tested for efficacy.

In another embodiment of a method for preparing the catalyst described herein, a functionalized imprinting molecule can be employed. A functionalized imprinting molecule is an imprinting molecule that has been impermanently bound to a poly-functional linker through, for example, an ester linkage, sulfonic acid ester linkage, a carbamate (urethane), or a carbonate linkage.

Examples of poly-functional linkers include, but are not limited to, compounds of Formulas VIII-XI. In each of these compounds, $R^1$ is as described herein previously. $G^2$ is optional such that when $G^2$ is absent, a single bond is formed between the carbon and silicon shown linked to $G^2$. When present, $G^2$ is $C^1$-$C^6$ alkyl. $G^3$ can be O or N.

Formula VIII

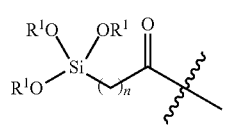

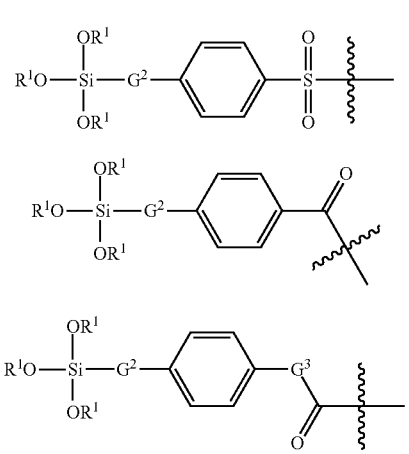

Formula IX

Formula X

Formula XI

Although the silicon species in each of the compounds according to Formulas IX-XI are shown as para substituted, compounds of Formulas IX-XI can be functionalized with copies of the para Si functionality at one or both meta positions instead. Alternatively, the phenyl ring can be para Si substituted as shown, with the phenyl ring further functionalized with the Si group present at the para position at one or both ortho positions, provided sterics permit.

The poly-functionalized linkers can be used in the synthesis of a biomimetic catalyst according to the following procedure. First, a poly-functionalized linker precursor, such as an activated ester, acid chloride, sulfonyl chloride (e.g. 2-(4-chlorosulfonylphenyl)ethyltrimethoxysilane), isocyanate, or other appropriately reactive species is reacted with a free alcohol on an imprinting molecule, such as, for example cellobiose. The resulting product is a functionalized imprinting molecule. The number of linkers that can be attached to a given imprinting molecule will be determined by the reactivity of the linker precursor, the nucleophilicity of free alcohol(s) on the imprinting molecule, and steric interactions in and around the nucleophilic alcohol(s).

The functionalized imprinting molecule is then mixed with at least one tetraorthosilicate according to at least one of Formulas I, II, III or IV and, optionally, at least one silane according to at least one of Formulas V, VI, or VII. The reagents are then polymerized using an acidic catalyst. Solvents and catalysts useful for this polymerization have been identified herein previously. The molar ratios of the various components can range from about 100:20:80 to about 100:95:5, including all whole or partial increments there between. Ratios are presented as molar amounts of tetraorthosilicate:silane:functionalized imprinting molecule.

Once the polymerization is complete, the silica matrix can be isolated and milled according to the procedures set forth elsewhere herein. Subsequently, the imprinting molecule must be excised from the matrix. This can be accomplished via hydrolysis of the various carbonate, carbamate (urethane), carboxylic, and sulfonate esters binding the imprinting molecule to the silica matrix. Hydrolysis can be accomplished by using strongly acidic or basic conditions. The silica matrix can then be isolated from the imprinting molecule using any of the drying/burning techniques discussed herein previously. Subsequent milling is optional. The activity of the optionally milled catalyst can be assayed using known techniques.

When a carbamate (urethane) linker is utilized, the resulting polymer (after hydrolysis) will contain a substituted aniline in the active site. In certain embodiments, the aniline can be allowed to remain. In other embodiments, however, the amine of the aniline can be diazotized using a known reagent, such as nitrosonium tetrafluoroborate ($NOBF_4$) or sodium nitrite/$H_2SO_4$, and converted to a phenol, nitrile, or halide. If converted to a nitrile, the nitrile can subsequently be hydrolyzed to a carboxylic acid. If converted to a halide, the compound can be converted into a Grignard reagent and subsequently quenched with $CO_2$ to form a carboxylic acid. Alternatively, the halide can be cross coupled with another reagent using known Pd or Pt mediated cross coupling reactions.

The benefits of using the poly-functionalized linker, as compared to the non-linked procedures (described elsewhere herein) are manifest. Specifically, when the functionalized imprinting molecule is polymerized with the tetraorthosilieate and silane, the acidic residues that will subsequently be used to hydrolyze glucose substrates are positioned in the cavity created by the imprinting molecule in such as way as to make it more likely that a glucose substrate will be hydrolyzed to glucose.

Hydrolysis of a Glucose Substrate

Having prepared a catalyst as described above, the catalyst can be used according to any of the following procedures. In a first embodiment, the catalyst and glucose substrate can be dissolved in a solvent. Appropriate solvents include, for example, ionic liquids, examples of which were described previously herein. Ionic liquids, unlike many organic solvents are capable of solvating glucose substrates such as cellulose and its derivatives. Although ionic liquids are useful, standard organic solvents such as water, N,N-DMF, methanol, ethanol, isopropanol, ethyl acetate, isopropyl acetate, dichloromethane, chloroform, carbon tetrachloride, NMP, tetrahydrofuran (THF), acetonitrile, as well as mixtures thereof, can also be used. The utility of any of the above described solvents will, however, depend on how soluble (or insoluble) the glucose substrate is in the solvent as well as the temperature at which the reaction is run.

Figure 7:
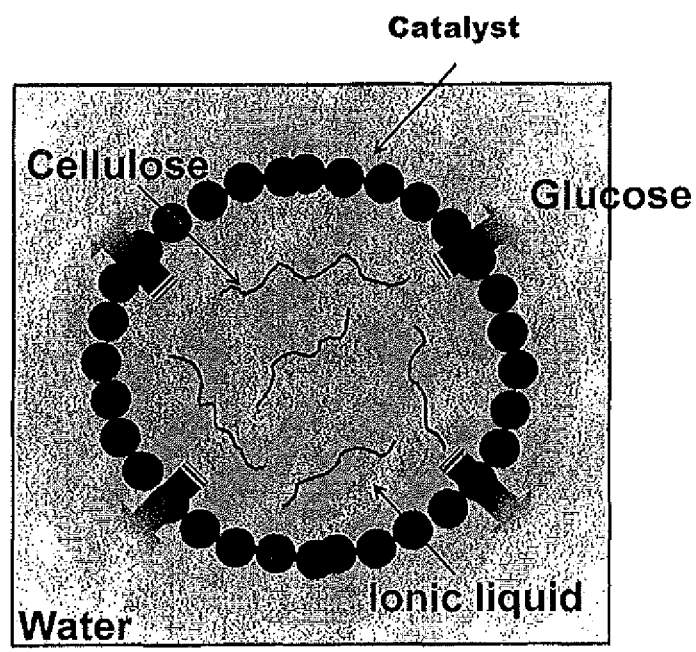
FIG. 7 is a graphical representation of a glucose producing microreactor in an aqueous environment.

In certain embodiments, the hydrolysis reaction can be performed using an ionic liquid in combination with another solvent, such as water, methanol, ethanol, isopropanol, or other higher alcohol. In particular embodiments, the solvent combination is an ionic liquid and water. Without wishing to be bound to any particular theory, it is believed that when an ionic liquid and water are used as the solvents, and the amount of ionic liquid used is smaller than the amount of water, the catalyst will sequester the ionic liquids in micelle like structures, creating an emulsion wherein the micelle-like structures are microreactors for the hydrolysis of a glucose substrate. It is believed, that the catalyst membrane will be semi-permeable such that glucose will be able to exit the microreactor after glucose substrate hydrolysis. See, FIG. 7. These microreactors will enable specific binding of individual cellulose polymers (or other glucose substrate) to catalytic domains present on and/or in the catalyst and, at the same time, allow for the subsequent release of glucose based on glucose's high solubility in the aqueous phase. The catalysts can be readily recycled through emulsion destabilization and re-emulsification process to achieve a high rate of cellulose conversion.

In alternative embodiments, the ionic liquid can be used in an amount (volume) in excess of the quantity of water used. Without wishing to be bound to any particular theory, it is believed that in this configuration, water will be sequestered by the catalyst to form micelle like structures.

Catalysts would take place at the ionic liquid/catalyst interface and the glucose thus produced would migrate into the aqueous layer.

The hydrolysis reaction can be run at temperatures ranging from about 40° C. to about 400° C., including all whole and partial increments there between. In one embodiment, the hydrolysis reaction is run at about 100 to about 150° C. The temperature at which the reaction will be run will dictate which solvents can be used. Catalyst loading in a given reaction can be from 0.01 weight percent to 50 weight percent based on the weight of glucose substrate present in the reaction. In preferred embodiments, the catalyst loading is less than about 10 weight percent, even more preferably less than about 5 weight percent and most preferably less than about 1 weight percent.

EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

MIP Surface Area

MIP surface area can be calculated using BET measurements. BET measurements were performed by placing a known quantity of catalyst in a tube filled with liquid $N_2$. Surface area was subsequently determined based on physical adsorption of krypton gas at liquid $N_2$ temperatures.

Example 1

Synthesis of a Cellobiose Imprinted Propylsulfonic Acid-Functionalized Silica

Cellobiose (1.6 g) was dissolved in water (52 mL) and HCl (8 ml, 1M). The reaction mixture was then heated to 50° C. for about 30 minutes. Subsequently, tetraethylorthosilicate (TEOS) (2.98 mL) was added and the mixture was stirred at 50° C. for about 3 hours. Subsequently, 0.075 equivalents ("7.5% acid") of MPTMS ((3-mercaptopropyl) trimethoxysilane) (molar equivalents based on the molar amount of TEOS) and 4 equivalents of 30% aqueous $H_2O_2$ (based on the molar amount of MPTMS) were added. The mixture was then heated for about 24 hours at 100° C. in an oven to form an MIP.

Next, cellobiose in the MIP polymeric matrix was removed. Removal was accomplished by treating the MIP in refluxing ethanol for about 7 hours. After cooling, the resulting mixture was centrifuged. Ethanol containing cellobiose was decanted away from a solid mass that had collected due to centrifugation. The resultant solid was then re-suspended in clean ethanol, sonicated, and centrifuged again. The sonication/centrifugation procedure was repeated two more times.

BET surface area was calculated to be 390.2 $m^2/g$.

The above described procedure was also performed using 0.02 and 0.15 equivalents ("2% acid" and "15% acid," respectively) of MPTMS. Surface areas for these catalysts were not calculated.

Example 2

Synthesis of a Lactose Imprinted Propylsulfonic Acid-Functionalized Silica

The lactose imprinted MIP was prepared according to the procedure set forth for Example 1, using 2%, 7.5%, and 15% MPTMS, except that lactose (1.68 g) was used instead of cellobiose. BET surface area of the 7.5% MPTMS catalyst was calculated to be 409.2 $m^2/g$.

Example 3

Synthesis of a Non-Imprinted Propylsulfonic Acid-Functionalized Silica

The non-imprinted MIP was prepared according to the procedure set forth in Example 1, using 2%, 7.5%, and 15% MPTMS, except that no imprinting agent was added. BET surface area of the 7.5% MPTMS was calculated to be 394.1 $m^2/g$.

Example 4

Calculation of the Total Number of Acidic Sites

Figure 3:
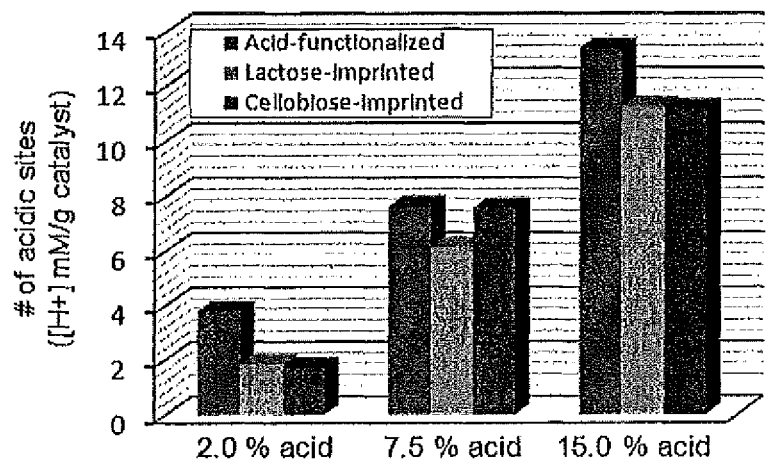
FIG. 3 is a graph representing the number of acidic sites in an MIP catalyst of the invention (mM[H+]/g catalyst).

A known mass of MIP was dissolved in a known volume of 0.1 M NaCl, the pH of which was recorded prior to addition of the MIP. The pH of the solution was allowed to equilibrate for several minutes, until stable. Subsequently, 0.01M NaOH was added to the solution dropwise, until the pH of the solution was equal to its pH prior to addition of the MIP. The volume of 0.01M NaOH added was recorded and the number of moles of acid were calculated. FIG. 3 is a graph showing the relative number of acidic sites (mM/g) in the 2%, 7.5%, and 15% MPTMS derived catalysts described in Examples 1, 2, and 3.

Example 5

Cellobiose Hydrolysis

Figure 4:
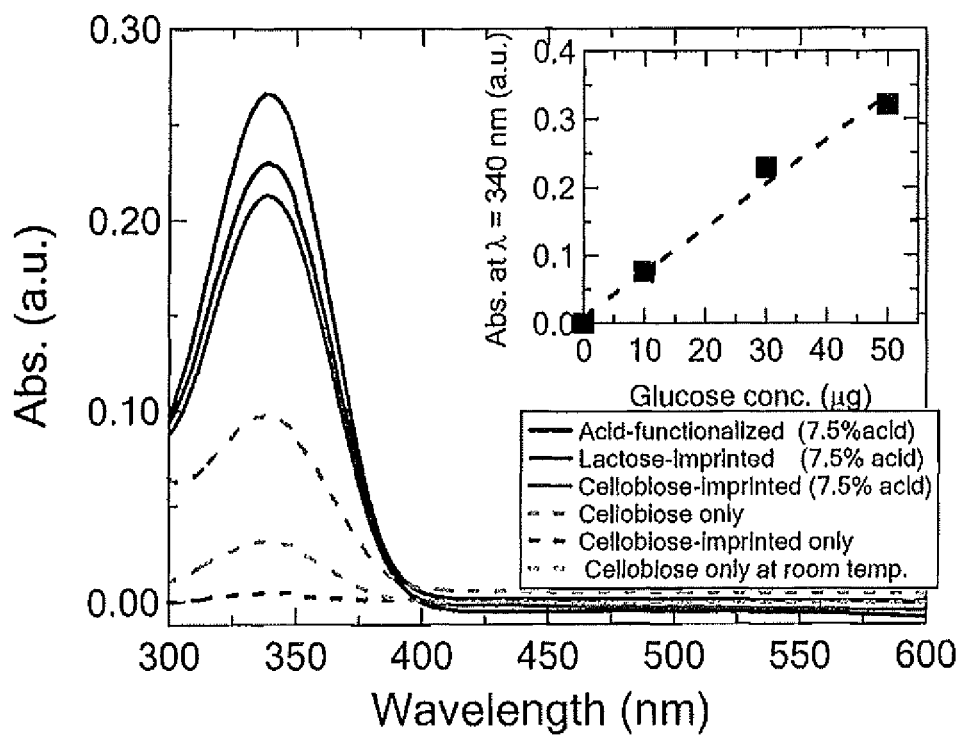
FIG. 4 is a graph depicting the activity of MIPs prepared using 7.5% MPTMS for the hydrolysis of cellobiose at 121° C.
Figure 5:
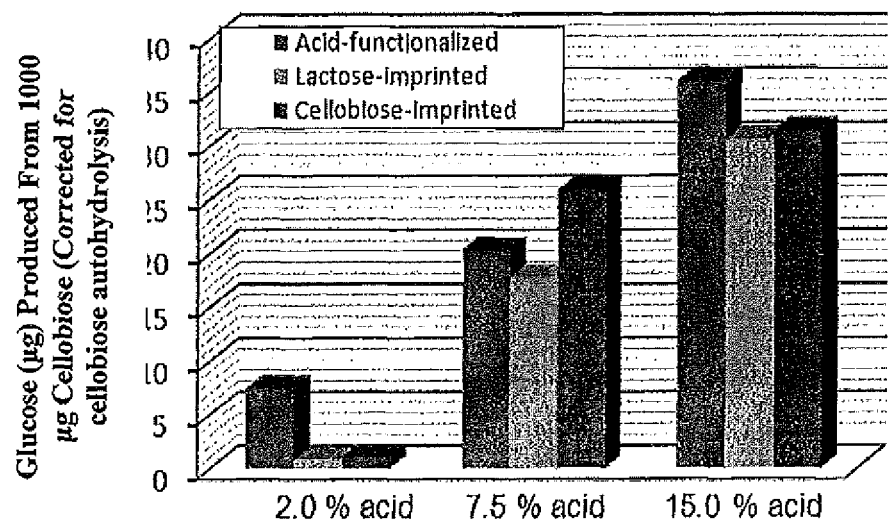
FIG. 5 is a graph depicting the quantity (μg) of glucose produced by the hydrolysis of cellobiose by various MIPs described herein at 121° C. (corrected to exclude contaminant glucose and glucose produced via the auto-hydrolysis of cellobiose).
Figure 6:
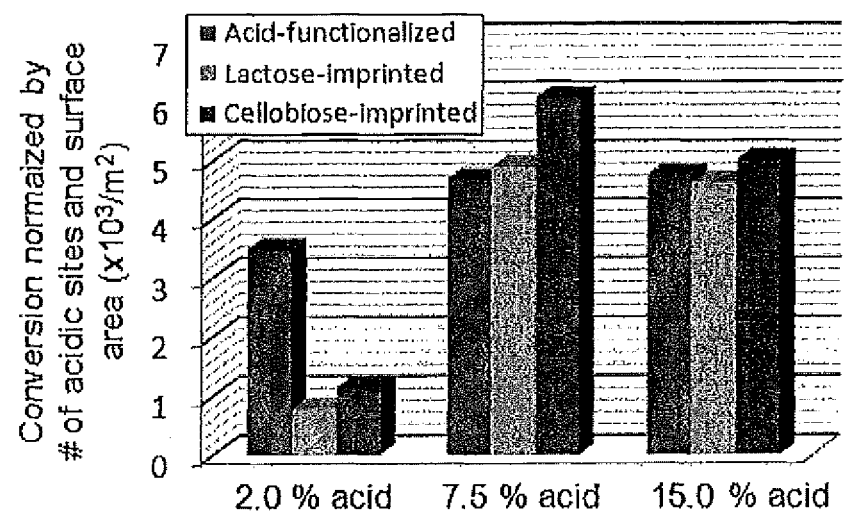
FIG. 6 is graph depicting the conversion of cellobiose to glucose, wherein the data have been normalized to account for the number of acidic sites and surface areas of the various MIPs used.

Cellobiose was hydrolyzed in the presence of the various catalysts prepared in Examples 1, 2, and 3. For each experiment, cellobiose (0.25 g) and catalyst (0.05 g) were added to water (25 mL). The mixture was then sonicated for 3 minutes at either 70 or 121° C. for 2 hours in an autoclave. Glucose was detected via UV at 340 nm using a glucose detection kit. The results using catalysts prepared with 7.5% MPTMS are shown in FIG. 4. For purposes of comparison, the figure further includes data corresponding to hydrolysis characteristics of cellobiose by itself (at room temperature), the hydrolysis characteristics of cellobiose by itself at 121° C., and the UV spectrum of the MIP by itself at reaction temperature.

The disclosures of each and every patent, patent application, and publication cited herein are hereby incorporated herein by reference in their entirety.

While the invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A biomimetic catalyst, said catalyst comprising:
   a polymeric silica matrix, wherein preparation of the matrix comprises reacting at least one tetraorthosilicate with at least one silane in the presence of an imprinting molecule to form said polymeric silica matrix impregnated with said imprinting molecule, and removing said imprinting molecule from said impregnated polymeric silica matrix via washing or burning;

wherein at least 1 mol percent of said at least one silane is an acid functionalized silane;
wherein said imprinting molecule is at least one selected from the group consisting of cellulose, cellobiose, linear oligomeric β(1-4) linked glucose chains longer than cellobiose but shorter than cellulose, carboxymethylcellulose, methylcellulose, hydropropylcellulose, linear and branched α-linked glucose oligomer and polymers, sucrose, lactose, trehalose, fructans, pectins, glycosaminoglycans, agar, gum Arabic, karageenan, glucose, and D-glucose 6-phosphate;
at least one active site imprinted into said matrix, wherein said active site binds and hydrolyzes at least one glucose substrate to glucose,
wherein said glucose substrate is at least one selected from the group consisting of cellulose, cellobiose, linear oligomeric β(1-4) linked glucose chains longer than cellobiose but shorter than cellulose, and linear and branched α-linked glucose oligomers and polymers, and
wherein at least one said acid functionalized silane is incorporated in said polymeric silica matrix and is present in said active site.

2. The biomimetic catalyst of claim 1, wherein said at least one acidic functionality is selected from the group consisting of a phenol, a carboxylic acid, and a sulfonic acid.

3. A method of preparing the biomimetic catalyst of claim 1, said method comprising:
reacting at least one tetraorthosilicate with at least one silane in the presence of an imprinting molecule to form a polymeric silica matrix impregnated with said imprinting molecule, wherein at least 1 mol percent of said at least one silane is an acid functionalized silane;
wherein said imprinting molecule is at least one selected from the group consisting of cellulose, cellobiose, linear oligomeric β(1-4) linked glucose chains longer than cellobiose but shorter than cellulose, carboxymethylcellulose, methylcellulose, hydropropylcellulose, linear and branched α-linked glucose oligomer and polymers, sucrose, lactose, trehalose, fructans, pectins, glycosaminoglycans, agar, gum Arabic, karageenan, glucose, and D-glucose 6-phosphate;
isolating said impregnated polymeric silica matrix; and
removing said imprinting molecule from said impregnated polymeric silica matrix via washing or burning to form a silica matrix imprinted with the structure of said imprinting molecule,
wherein said matrix comprises at least one active site,
wherein said active site comprises at least one said acid functionalized silane that is incorporated in said polymeric silica matrix and binds and hydrolyzes at least one glucose substrate to glucose,
wherein said glucose substrate is at least one selected from the group consisting of cellulose, cellobiose, linear oligomeric β(1-4) linked glucose chains longer than cellobiose but shorter than cellulose, and linear and branched α-linked glucose oligomers and polymers.

4. The method of claim 3, wherein said at least one tetraorthosilicate is selected from the group consisting of Formulas I, II, III and IV:

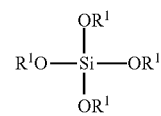
Formula I

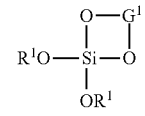
Formula II

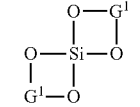
Formula III

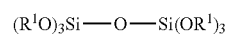
Formula IV wherein:
R$^1$ is, independently at each occurrence, C$_1$-C$_6$ alkyl or phenyl; and,
G$^1$ is C$_1$-C$_6$ alkyl,

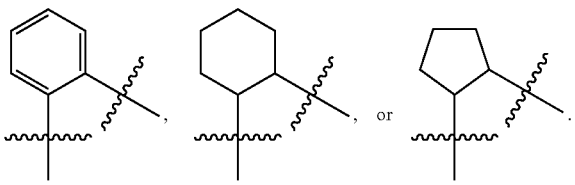 [SMILES: *c1ccccc1* ; *C1CCCCC1* ; *C1CCCC1*]

5. The method of claim 4, wherein R$^1$ is CH$_2$CH$_3$ at each occurrence.

6. The method of claim 3, wherein said at least one silane is a compound selected from the group consisting of Formulas V, VI, and VII:

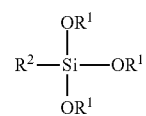
Formula V

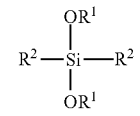
Formula VI

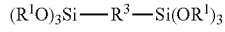
Formula VII wherein:
R$^1$ is, independently at each occurrence, C$_1$-C$_6$ alkyl or phenyl;
R$^2$ is, independently at each occurrence,

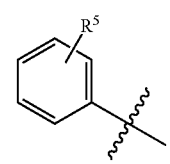

or $C_1$-$C_6$ alkyl optionally substituted with at least one substituent selected from the group consisting of $R^4$ and

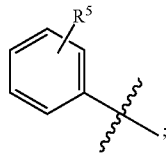

$R^3$ is $C_1$-$C_6$ alkyl optionally substituted with a substituent selected from the group consisting of $R^4$ and

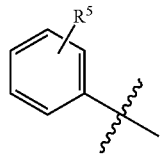

$R^4$ is SH, $NH_2$, OH, $CO_2H$, or $SO_3H$; and
$R^5$ is H, $NH_2$, OH, $SO_2Cl$, $CO_2H$, or $SO_3H$;
provided that when $R^4$ is SH or $R^5$ is $SO_2Cl$, the thiol or chlorosulfonyl groups are oxidized to $SO_3H$ after said removing of said imprinting molecule.

7. A method of producing glucose, said method comprising:
  dissolving a glucose substrate in a solvent;
  contacting said glucose substrate in said solvent with at least one biomimetic catalyst of claim 1 to hydrolyze said glucose substrate to glucose, said biomimetic catalyst comprising:
    a polymeric silica matrix, wherein preparation of said matrix comprises reacting at least one tetraorthosilicate with at least one silane in the presence of an imprinting molecule to form said polymeric silica matrix impregnated with said imprinting molecule, and removing said imprinting molecule from said impregnated polymeric silica matrix via washing or burning;
      wherein at least 1 mol percent of said at least one silane is an acid functionalized silane;
      wherein said imprinting molecule is at least one selected from the group consisting of cellulose, cellobiose, linear oligomeric β(1-4) linked glucose chains longer than cellobiose but shorter than cellulose, carboxymethylcellulose, methylcellulose, hydropropylcellulose, linear and branched α-linked glucose oligomer and polymers, sucrose, lactose, trehalose, fructans, pectins, glycosaminoglycans, agar, gum Arabic, karageenan, glucose, and D-glucose 6-phosphate;
    at least one active site imprinted into said matrix, wherein said active site binds and hydrolyzes at least one glucose substrate to glucose,
      wherein said glucose substrate is at least one selected from the group consisting of cellulose, cellobiose, linear oligomeric β(1-4) linked glucose chains longer than cellobiose but shorter than cellulose, and linear and branched α-linked glucose oligomers and polymers, and
      wherein at least one said acid functionalized silane is incorporated in said polymeric silica matrix and is present in said active site.

8. The method of claim 7, wherein said solvent is an ionic liquid or molten salt.

9. A method of producing ethanol, said method comprising:
  dissolving a glucose substrate in a solvent; wherein the glucose substrate is at least one selected from the group consisting of cellulose, cellobiose, linear oligomeric β(1-4) linked glucose chains longer than cellobiose but shorter than cellulose, and linear and branched α-linked glucose oligomers and polymers;
  contacting said glucose substrate in said solvent with at least one biomimetic catalyst of claim 1 to completely or partially hydrolyze said glucose substrate to glucose, said biomimetic catalyst comprising:
    a polymeric silica matrix, wherein preparation of said matrix comprises reacting at least one tetraorthosilicate with at least one silane in the presence of an imprinting molecule to form said polymeric silica matrix impregnated with said imprinting molecule, and removing said imprinting molecule from said impregnated polymeric silica matrix via washing or burning;
      wherein at least 1 mol percent of said at least one silane is an acid functionalized silane;
      wherein said imprinting molecule is at least one selected from the group consisting of cellulose, cellobiose, linear oligomeric β(1-4) linked glucose chains longer than cellobiose but shorter than cellulose, carboxymethylcellulose, methylcellulose, hydropropylcellulose, linear and branched α-linked glucose oligomer and polymers, sucrose, lactose, trehalose, fructans, pectins, glycosaminoglycans, agar, gum Arabic, karageenan, glucose, and D-glucose 6-phosphate;
    at least one active site imprinted into said matrix, wherein said active site binds and hydrolyzes said glucose substrate to glucose, and wherein at least one said acid functionalized silane is incorporated in said polymeric silica matrix and is present in said active site;
  isolating said glucose; and
  converting said glucose to ethanol.

* * * * *